United States Patent [19]

McGuire

[11] Patent Number: 5,391,169
[45] Date of Patent: Feb. 21, 1995

[54] PATELLAR TENDON HARVESTER

[76] Inventor: David A. McGuire, 3418 Lakeside Dr., Anchorage, Ala. 99515

[21] Appl. No.: 19,546

[22] Filed: Feb. 19, 1993

Related U.S. Application Data

[63] Continuation-in-part of Ser. No. 806,906, Dec. 13, 1991, Pat. No. 5,257,996.

[51] Int. Cl.$^6$ .............. A61B 17/00; A61F 5/00; B26B 3/00
[52] U.S. Cl. .............. 606/79; 606/86; 30/299
[58] Field of Search .............. 606/79, 80, 82, 83, 606/84, 86, 87, 88; 30/147, 148, 299, 346, 355, 356, 357

[56] References Cited

U.S. PATENT DOCUMENTS

| | | | |
|---|---|---|---|
| 1,584,021 | 5/1926 | Dunn | 30/299 |
| 1,920,821 | 8/1933 | Wassenaar | 606/86 |
| 2,022,954 | 12/1935 | Cook | 30/299 |
| 2,134,839 | 11/1938 | Perkins | 30/304 |
| 2,250,237 | 7/1941 | Schwartzkopf | 30/304 |
| 2,397,875 | 4/1946 | Marshaus | 30/304 |
| 2,882,599 | 4/1959 | Martin | 30/356 |
| 3,221,744 | 12/1965 | Stryker | 606/84 |
| 3,415,251 | 12/1968 | Knapp et al. | 128/305 |
| 3,452,754 | 7/1969 | Stayer | 128/305 |
| 3,915,169 | 10/1975 | McGuire | 128/305 |
| 4,067,340 | 1/1978 | Le Noir | 128/305 |
| 4,239,045 | 12/1980 | Schlein | 128/305 |
| 4,472,879 | 9/1984 | Sizemore, Jr. | 30/304 |
| 4,617,930 | 10/1986 | Saunders | 602/82 |
| 4,651,735 | 3/1987 | Berger | 128/304 |
| 4,665,915 | 5/1987 | Grollimund | 128/305.5 |
| 4,686,978 | 8/1987 | Wadsworth | 128/303 R |
| 4,708,147 | 11/1987 | Haaga | 128/753 |
| 4,881,537 | 11/1989 | Henning | 606/84 |
| 5,026,385 | 6/1991 | Schutte et al. | 606/167 |
| 5,100,391 | 3/1992 | Schutte et al. | 606/167 |
| 5,163,939 | 11/1992 | Winston | 606/79 |
| 5,217,463 | 6/1993 | Mikhail | 606/86 |
| 5,222,951 | 6/1993 | Abidin | 128/20 |

FOREIGN PATENT DOCUMENTS

| | | | |
|---|---|---|---|
| 1072361 | 9/1954 | France | |
| 2626165 | 7/1989 | France | 606/84 |

OTHER PUBLICATIONS

"ACL Graft Knife," advertisement, (Date unknown).
"Surgical Technique," advertisement (Date unknown).
Memorandum dated Sep. 28, 1987, from Rizzuti to Lee.
Notes on letterhead of Joseph Feinberg, M.D., and B. Donald Sklansk, M.D. (Date unknown), 2 pages.

*Primary Examiner*—Michael A. Brown

[57] ABSTRACT

A patellar tendon harvester having a two-tined fork connected to a handle. A pair of blades are supported in side-by-side relationship from the two-tined fork. Each blade has a concave cutting edge. A bent stem portion may be provided between the handle and the two-tined fork. The patellar tendon harvester may be used to harvest a patellar tendon through incisions of less than three centimeters in length.

20 Claims, 2 Drawing Sheets

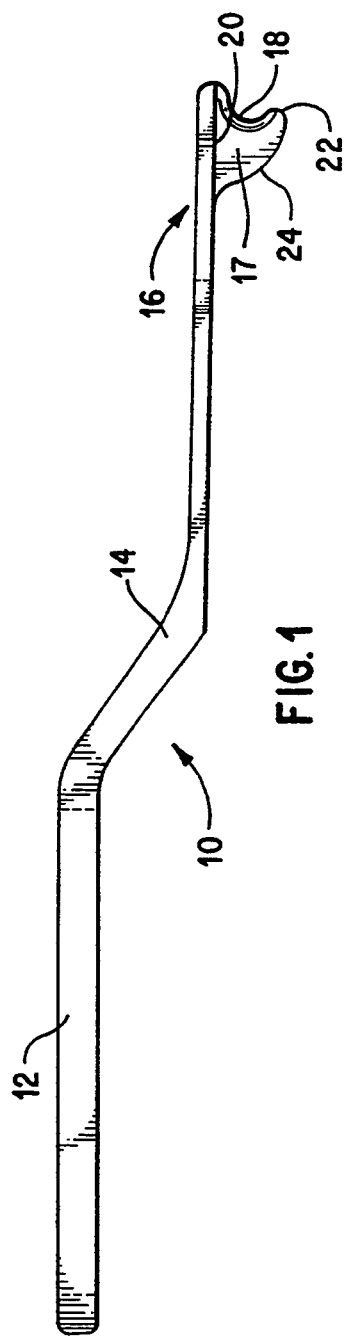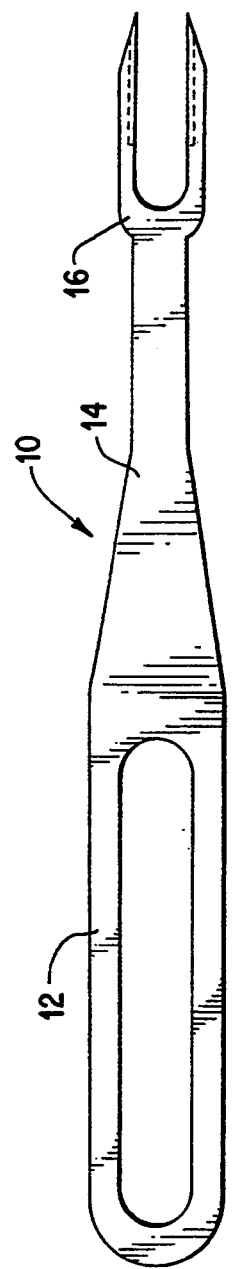

PATELLAR TENDON HARVESTER

This application is a continuation-in-part of U.S. patent application Ser. No. 07/806,906, filed Dec. 13, 1991, now U.S. Pat. No. 5,257,996. This related application is hereby incorporated herein by reference.

BACKGROUND OF THE INVENTION

The present invention is directed to a double-bladed meniscotome for harvesting a strip of patellar tendon and the method for performing same.

A bone-patellar tendon-bone graft is harvested for use in anterior cruciate ligament reconstruction. Schutte et al. have disclosed in U.S. Pat. No. 5,026,385 a double-bladed scalpel for simultaneously cutting along opposite sides of the patellar tendon. A scalpel, however, has its cutting edge along the bottom edge of the knife blade. Cutting is performed by pushing down against the blades to force the blades into the tendon being cut. When the double-bladed scalpel is pressed against a bone at the end of the tendon graft the scalpel blades have a tendency to splay apart. The Schutte et al. design provides structure for avoiding the separation of the scalpel blades during cutting. In using a scalpel as disclosed by Schutte et al., the surgeon's fingers rest up near the blades. As such, incisions totalling over about four inches must be made in a knee to permit a surgeon to use the Schutte et al. scalpel to harvest the patellar tendon autograft.

Another device that has been used for cutting the patellar tendon graft is a Smillie meniscotome. The Smillie meniscotome has a single concave cutting edge mounted on a straight handle. While a smaller incision is capable of accommodating the Smillie meniscotome during patellar tendon harvesting, it is difficult to make sure that the tendon fibers attached to one bone block are the same fibers connected to the other bone block. The single bladed Smillie meniscotome requires a separate cutting operation along each side of the tendon. As such, it is possible that only a few of the tendon fibers in the graft hold the two bone blocks together.

SUMMARY OF THE INVENTION

The present invention is directed to a patellar tendon harvester formed on a handle supporting a two-tined fork. A blade having a concave cutting edge facing forward of the handle is mounted on each tine of the fork. The blades are supported side-by-side substantially perpendicular to an imaginary plane that includes the two tines of the fork. A bent stem may be included between the handle and the fork connecting the handle to the fork and may maintain the handle and fork parallel to one another. The blades may be further modified so as to be curved toward each other.

A patellar tendon is harvested in accordance with the present invention by first making a vertical incision of less than three centimeters in length medial to the tibial tubercle and distal to the joint line. A vertical patellar incision of less than three centimeters is made. A saw is used to create a first bone block. The patellar tendon harvester is inserted through one of the incisions and pushed from the bone block along the patellar tendon to a second bone. An electrocautery device may be used to mark the second bone at the ends of the patellar tendon harvester. The saw cuts for the second bone block are thus advantageously oriented with respect to the two blades of the patellar tendon harvester that have been pushed along the tendon fibers. It will therefore be more likely that the fibers connected to the first bone block are primarily the fibers connected to the second bone block. The second bone block is harvested and the bone-tendon-bone graft is removed.

The patellar tendon may be harvested in accordance with the present invention through two incisions of less than three centimeters each. Other objects and advantages of the present invention will become apparent during the following description of the presently preferred embodiments of the invention taken in conjunction with the drawings.

BRIEF DESCRIPTION OF THE DRAWINGS

FIG. 1 is a side view of the patellar tendon harvester of the present invention.

FIG. 2 is a plan view of the patellar tendon harvester of FIG. 1.

DETAILED DESCRIPTION OF THE PREFERRED EMBODIMENTS

Figure 3:
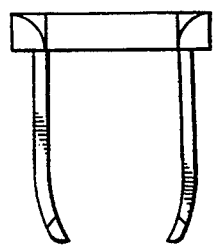
FIG. 3 is an end view of an alternate embodiment of the patellar tendon harvester.

Referring now to the drawings, a patellar tendon harvester 10 of the present invention is shown in FIGS. 1 and 2. At the rear end of the harvester is a handle portion 12. The handle of the embodiment in the drawings is a flat loop. The handle portion 12 is used by the surgeon for grasping the instrument. Other handle designs may be substituted for the flat loop. The flat loop is presently preferred because of its simplicity of manufacture. The harvester may be an integral structure of forged stainless steel. The handle portion 12 is connected by a bent stem portion 14 to a two-tined fork 16. The two-tined fork 16 is flat across an imaginary plane. In the presently preferred embodiment, the flat imaginary plane of the two-tined fork 16 is maintained parallel to the handle 12 by the bent stem portion 14. By providing a bend in the stem of the instrument, a surgeon is able to insert the harvester within the incision and control the patellar tendon harvester from outside the incision. Moreover, the small incision can be less than three centimeters. In accordance with the presently preferred embodiment the handle portion 12 is 2.4 centimeters wide, 10 centimeters long, and about 0.7 centimeters thick. The stem 14 includes a slanted portion approximately four centimeters long and a portion that is parallel to the handle that is about four centimeters long, one centimeter wide, and three millimeters thick. The two tines of the fork 16 are four centimeters long and each tine is three millimeters wide and three millimeters thick. The inner edges of the tines in the fork 16 are separated by a distance determined by the width of the desired tendon graft. Therefore, typical separation distances are nine, ten, or eleven millimeters.

A pair of blades 17 is mounted on the tines of the fork 16. The blades 17 project from the tines of the fork perpendicular to the imaginary plane of the two-tined fork 16. The two blades 17 extend side-by-side, each having a cutting edge facing forward from the handle. The cutting edge 18 of each blade is preferably concave. Each blade 17 includes a top edge 20 which is supported along the tine of the fork 16. The cutting edge 18 extends from the top edge 20 of the blade to a tip 22 of the cutting blade. A rear edge of each blade extends from the tip 22 to the top edge 20 of the blade. The cutting edge 18 is on the flat inner-facing face of the blade. In an integral stainless steel harvester, the cutting edge 18 is made after the forging process by using a sharpening process to bevel the cutting edge 18 on the outer face of the blade. Thus, the inner face of the blade is flat, while the outer face of the blade includes the bevel of the cutting edge 18.

The pair of blades 17 are arranged in side-by-side relationship on the two-tined fork so that the concave cutting edge of each blade faces forward of the handle and is located above the tip of each blade. Thus, with the blades suspended beneath the two-tined fork 16, the tip 22 of each blade is the lowermost portion of the blade. The blades of the embodiment of FIGS. 1 and 2 are flat and parallel to one another. In accordance with an alternate embodiment shown in FIG. 3, the blades may be curved towards one another. For both embodiments, the tips of the blades are buffed smooth with no sharp transitions between the tip 22 and the cutting edge 18. The concave cutting edges of the blades of both embodiments advantageously guide the tissue being cut toward the middle of the blade and away from the tip. This allows for cleavage of the tendon to occur with a single pass with very little deviation and minimal damage, if any, to the surrounding tissues. By curving the blade surfaces toward one another as shown in FIG. 3, it is desired to improve the cleavage function of the tendon harvester.

Rather than fixedly mounting the blades on the tines of the fork as in the solid metal integral embodiment of the tendon harvester, detachable blades may be used. In this case, an attachment mechanism of conventional design is located on each tine of the fork. The detachable blades are disposable. The blades are mounted onto the tines of the fork in the same arrangement as described above for the fixed blades. The handle and fork may be made of plastic rather than metal, thereby making disposibility of the entire tendon harvester feasible.

Figure 4:
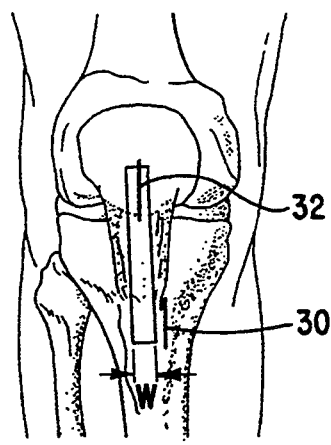
FIG. 4 is an illustration of the site on a knee where incisions are made for a bone-patellar tendon-bone graft.

The method for harvesting a patellar tendon graft shall now be described. A 2.5 centimeter vertical incision 30 is made one centimeter medial to the tibial tubercle and two centimeters distal to the joint line. Smaller incisions such as this provide for reduced invasiveness, less scarring and generally less pain. Also, in the event of scarring, a smaller incision results in a scar that is less noticeable. Thus, it is most advantageous for the incisions to be small, less than about three centimeters for example. Similarly, a patellar incision 32 of 2.5 centimeters is made beginning at the distal pole of the patella and extending proximally over the midline of the patella. The vertical incisions have cosmetic advantages and produce less pain and reduce the incidence of arthrofibrosis. The positioning of these incisions is shown in FIG. 4. The graft width w as desired is measured on the tibial tubercle. An electrocautery device, such as a Bovee device, is used to mark the middle third width to be harvested. Normally, the graft takes a bone block of ten millimeters width from the tibial tubercle and a bone block of eleven millimeters in width from the patella. The widths vary depending upon the size of the patient.

Figure 5:
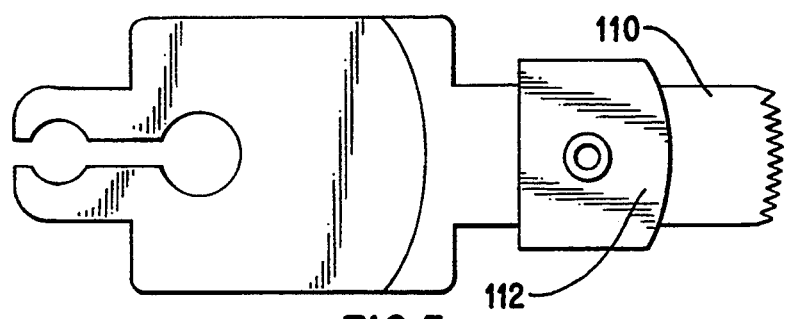
FIG. 5 is a side view of an oscillating saw blade.

A patellar tendon harvest may be taken through the vertical incisions 30 and 32 and may be harvested with an oscillating saw. The presently preferred oscillating saw blade 110 and its use described herein are illustrated in FIG. 5. The saw blade 110 gets mounted on a camshaft perpendicular to that camshaft. In operation, the camshaft rotates in a partial turn clockwise by a small angular distance and then rotates in a partial turn counterclockwise by an equal small angular distance. The camshaft rotates back and forth rapidly, causing the saw blade to oscillate back and forth rapidly in the plane of the blade. The cutting edge of the saw blade has a concave profile, forming an arc on a circle centered on the camshaft's axis of rotation. Further, the saw blade in this embodiment advantageously includes a collared stop 112. The collared stop 112 has a stopping edge in the shape of an arc on a circle concentric with the circle coincident with the arc of the saw blade cutting edge. The presently preferred distance between the cutting edge and the stopping edge is 8 mm. The stop 112 uniformly limits the depth to which the saw blade can cut all along a cutting operation. Therefore a kerf (i.e., a cut) of uniform depth is obtained. A vertical edge at the end of the cut is formed by guiding the saw vertically down into the bone until the stop collar meets the bone. If desired, the portion of the side of the saw blade lying between the cutting edge and the stop collar may be coincident with radii extending from the camshaft's axis of rotation. The sides are then normal to the cutting edge. Such a blade can make a vertical edge at the end of a cut all the way down to the bottom of the cut. Whereas in the embodiment shown in FIG. 1 the arc of the cutting edge is a relatively small angular distance, the sides are approximately normal to the cutting edge, and therefore permit cutting a substantially rectangular kerf.

The tibial tubercle portion 220 may be harvested first with a width of 10 mm. The initial cut is made by the oscillating saw vertically through the cortex and is then angled. By angling the cuts along both sides of the bone block, a V-shaped block may be formed. Preferably however, the angles are made at approximately 60° from horizontal and the transverse cut is also angled. An osteotome, or similar chisel device, is inserted in the transverse cut to pry out the bone block which will have a trapezoidal shape. The bottom surface is formed by a controlled fracture when the osteotome lifts the bone weakened by the angled cuts. It is particularly important that the cuts by the oscillating saw be placed precisely to avoid extending beyond the region of bone to be harvested because the bone can be excessively weakened in that it becomes more susceptible to fracture. If a conventional oscillating saw is used, the kerf will not be of uniform depth along its length, nor will the opposing ends of the cut have vertical walls. Instead, the opposing ends will typically have a gradual taper to the full cut depth, a situation requiring that the kerf must extend beyond the region of the bone to be harvested, with the result of greater risk of fracture. However, by utilizing Dr. McGuire's design of oscillating saw described above, the kerf may have a uniform depth and vertical opposing ends, and thus provides a greatly reduced risk of fracture.

After creating the bone block, the double-bladed patellar tendon harvester of the present invention is inserted through the tibial incision. The tips of the blades are inserted about the bone block and the patellar tendon harvester is pushed forward so that the blades follow the fibers of the patellar tendon vertically from the tibial tubercle to the patella. The double-bladed patellar tendon harvester advantageously follows the tendon fibers from both edges of the tibial bone block. The elongated fork and stem follow the tendon beneath the skin while the surgeon holds the handle 12 outside of the incision. The bent portion 14 of the patellar harvester permits the fork 16 to extend beneath the skin all the way to the patella while the surgeon holds the handle 12 outside of the incision.

When the patellar tendon harvester has been fully inserted through the tendon to the patella, the ends of the two-tined fork provide a convenient means for marking the patellar portion so that it is properly centered about the tendon fibers connected to the tibial bone block. The electrocautery device can mark the patella using the tines of the patellar tendon harvester as a guide. The patellar tendon harvester is then removed and the patellar portion is harvested with the angle of the saw at 60 degrees and at a depth of approximately eight millimeters. A horizontal saw cut is made approximately four to five millimeters distal to the proximal pole of the patella. An osteotome or similar device is used to pry up the bone block. Any sharp edges in the trough of the patellar defect may be contoured with a rongeur. The patellar defect is filled with bone chips removed from the bone blocks. The bone-tendon-bone graft is removed through one of the incisions, completing the harvest of the patellar tendon.

Of course, it should be understood that various changes and modifications to the preferred embodiments described above will be apparent to those skilled in the art. For example, any number of various handle designs may be used on the patellar tendon harvester. Likewise, the angle and shape of the stem portion may be varied. Moreover, rather than using an integral handle stem and fork and blade design, the present invention may be made from several parts or components, which may include disposable blades. These and other changes may be made without departing from the spirit and scope of the invention and without diminishing its attendant advantages. It is therefore intended that such changes and modifications be covered by the following claims:

I claim:

1. A tendon harvester comprising:
   a handle;
   a two-tined fork extending forward of said handle; and
   a pair of blades mounted on the tines of said fork such that each blade projects from one of the tines of said fork with a sharp concave cutting edge of said each blade facing forward, said blades mounted so as to extend side-by-side substantially perpendicular to an imaginary plane including the two tines of said fork.

2. The tendon harvester of claim 1 wherein said handle is flat and parallel to the imaginary plane including the two tines of said fork.

3. The tendon harvester of claim 1 further comprising a bent stem connected between said handle and said two-tined fork such that said handle and said pair of blades when mounted are on opposite sides of the imaginary plane including the two tines of said fork.

4. The tendon harvester of claim 3 wherein said handle is flat and parallel to the imaginary plane including the two tines of said fork.

5. The tendon harvester of claim 1 wherein each of said blades are flat and parallel to one another.

6. The tendon harvester of claim 1 wherein the surfaces of the two blades are curved toward each other.

7. The tendon harvester of claim 1 wherein said pair of blades are solidly affixed to the tines of said fork.

8. The tendon harvester of claim 1 wherein said pair of blades are removably mounted to the tines of said fork.

9. A tendon harvester comprising: a pair of blades, each blade having a tip, a top edge, a rear edge extending from the tip to the top edge and a front concave cutting edge extending from the tip to the top edge; a handle having a rear end and a front end; and means, connected to the front end of said handle, for suspending said pair of blades in side-by-side relation from the top edges of said blades so that the concave cutting edge of each blade faces forward above the tip of said each blade.

10. The tendon harvester of claim 9 wherein said suspending means comprises a two-tined fork.

11. The tendon harvester of claim 10 wherein said suspending means further comprises a bent stem connected between the front end of said handle and said two-tined fork such that said handle is above and parallel to said two-tined fork.

12. The tendon harvester of claim 10 wherein said suspending means further comprises means for removably attaching said pair of blades to the two-tined fork.

13. The tendon harvester of claim 10 wherein said pair of blades are firmly affixed to the tines of the fork.

14. The tendon harvester of claim 9 wherein each of said blades in said pair of blades is flat and parallel to one another.

15. The tendon harvester of claim 9 wherein the tip of each of said blades in said pair of blades is curved in a direction towards the tip of the other of said blades in said pair of blades.

16. A tendon harvester comprising:
   a handle;
   a two-tined fork extending forward of said handle; and
   means for removably mounting a pair of blades on the tines of said fork such that each blade projects from one of the tines of said fork with a sharp concave cutting edge of said each blade facing forward, said blades mounted so as to extend side-by-side substantially perpendicular to an imaginary plane including the two tines of said fork.

17. The tendon harvester of claim 16 further comprising a bent stem connected between said handle and said two-tined fork such that said handle and said pair of blades when mounted are on opposite sides of the imaginary plane including the two tines of said fork.

18. The tendon harvester of claim 17 wherein said handle is flat and parallel to the imaginary plane including the two tines of said fork.

19. The tendon harvester of claim 16 wherein each of said blades are flat and parallel to one another.

20. The tendon harvester of claim 16 wherein the surfaces of the two blades are curved toward each other.

* * * * *